United States Patent [19]

Hupp

[11] Patent Number: 4,520,206

[45] Date of Patent: May 28, 1985

[54] PROCESS FOR PREPARING MALEIMIDE

[75] Inventor: Stephen S. Hupp, Dublin, Ohio

[73] Assignee: Ashland Oil, Inc., Ashland, Ky.

[21] Appl. No.: 583,924

[22] Filed: Feb. 27, 1984

[51] Int. Cl.$^3$ .......................................... C07D 207/267
[52] U.S. Cl. ..................................... 548/548; 548/552
[58] Field of Search ............................... 548/548, 508

[56] References Cited

U.S. PATENT DOCUMENTS 3,984,434  10/1976  O'Murchû ........................ 548/508

FOREIGN PATENT DOCUMENTS 684736  4/1964  Canada ................................. 548/508
128371  7/1983  Japan ................................... 548/508
569568  8/1977  U.S.S.R. .

Primary Examiner—Richard L. Raymond
Assistant Examiner—D. B. Springer
Attorney, Agent, or Firm—John F. Jones

[57] ABSTRACT

A process for the preparation of maleimide by the vapor phase oxydehydrogenation of succinimide over a heterogeneous catalyst composed of copper, phosphorous, vanadium, molybdenum and oxygen is described.

4 Claims, No Drawings

PROCESS FOR PREPARING MALEIMIDE

PROCESS FOR PREPARING MALEIMIDE

This invention relates to a method for the preparation of maleimide and more particularly pertains to the oxidative dehydrogenation of succinimide in the vapor phase over a specified heterogeneous catalyst to form maleimide in good yields.

Maleimide, also known as maleic acid amide, is a well-known material which has been used as a monomer in the manufacture of homopolymers and copolymers and also as a fungicide and bactericide. Because of the lack of prior methods for the production of maleimide in good yields and resultant high cost, it is believed that this material has not been utilized as fully as it might have been in the past.

Heretofore, maleimide has been prepared by the ammonolysis of maleic anhydride followed by dehydration over dehydration catalysts as in British Pat. No. 1,123,515. Maleimide has also been prepared by the ammoxidation of butadiene as disclosed in Japanese Pat. No. 42-2693 (1967), and by the oxidative dehydrogenation of succinimide over vanadium oxide or vanadium oxide-titanium dioxide catalyst as in USSR Inventor's Certificate No. 569,568.

I have discovered that maleimide can be prepared in good yields by the oxidative dehydrogenation of succinimide (succinic acid amide) in the presence of air and water and in the presence of a heterogeneous catalyst having the formula $Cu_aP_bV_xMo_yO_z$ wherein a is 0.002 to 0.2, b is 0.01 to 1, x is 0.01 to 1, y is 1.2 and z is the value corresponding to the average valences of the elements in the oxidation states in which they exist in the catalyst, in the temperature range of from 300° to 550° C., and in the pressure range of from 0.1 to 10 atmospheres.

In my process, the succinimide:air:water molar rations can vary from 1:0.1:1 to 1:5:50, respectively.

The heterogeneous catalysts of my invention are preferably calcined at a temperature in the range of from 300° C. to 600° C. For an hour or more before being used in the oxydehydrogenation of succinimide to maleimide.

The process of this invention is further illustrated in the following representative examples.

EXAMPLE 1

A catalyst having the emperical formula $Cu_{0.021}P_{0.11}V_{0.10}Mo_{1.2}O_z$ was prepared by mixing together 195 g. of $(NH_4)_2Mo_2O_7$, 12 g of concentrated $H_3PO_4$(85%), 11.66 g of $NH_4VO_3$, 4.8 g of $Cu(NO_3)_2.3H_2O$ and enough water to dissolve the solids. The solution was evaporated to dryness at 120° C. and calcined overnight at 450°.

EXAMPLE 2

The oxydehydrogenation of succinimide to maleimide was carried out in a stainless steel tube reactor 8" long having a 5/8" I.D. The reactor was charged with a mixture of the catalyst described in Example 1 (10 cc, 9.28 g) which was 12-20 mesh in size and 28.20 g of 12-20 mesh quartz chips. A solution of 26.8% by weight of succinimide and 0.1% hydroquinone (based on the weight of solution) in water was fed at a flow rate of 23.6 g/hr. with air at 77 cc/min. into the reactor. The reaction temperatures for several runs are given in the following table as well as yields of maleimide (MI) conversion of succinimide (SI) and selectivity of maleimide.

TABLE

| Reaction Temperature | MI Yield, % | SI Conversion, % | MI Selectivity, % |
| --- | --- | --- | --- |
| 403–407° C. | 12 | 17.2 | 69.8 |
| 460–468° C. | 18.2 | 62.0 | 29.3 |
| 487–500° C. | 26.5 | 70.8 | 30.4 |
| 496–510° C. | 21.7 | 96.6 | 22.5 |
| 518–527° C. | 28.5 | 98.1 | 29.0 |

I claim:

1. A process for the preparation of maleimide comprising subjecting a mixture of succinimide, air and water to oxidative dehydrogenation at a temperature in the range of from 300° to 550° C. over a catalyst having the formula $Cu_aP_bV_xMo_yO_z$ wherein a is 0.002 to 0.2, b is 0.01 to 1, x is 0.01 to 1, y is 1.2, and z is the value corresponding to average valances of the elements in the oxidation states in which they exist in the catalyst.

2. The process of claim 1 carried out in the pressure range of from 0.1 to 10 atmospheres.

3. The process of claim 2 wherein the mole ratios of succinimide: air: water are in the range of 1:0.1:1 to 1:5:50, respectively.

4. The process of claim 3 wherein the catalyst is $Cu_{0.021}P_{0.11}V_{0.10}Mo_{1.2}O_x$.

* * * * *